United States Patent [19]

Stöhr

[11] 4,243,318

[45] Jan. 6, 1981

[54] FLUORESCENCE ANALYSIS OF STAINED PARTICLES

[75] Inventor: Michael Stöhr, Heidelberg, Fed. Rep. of Germany

[73] Assignee: Deutsches Krebsforschungszentrum, Heidelberg, Fed. Rep. of Germany

[21] Appl. No.: 924,382

[22] Filed: Jul. 13, 1978

[30] Foreign Application Priority Data

Jul. 16, 1977 [DE] Fed. Rep. of Germany ....... 2732272

[51] Int. Cl.³ ............................................ G01J 21/64
[52] U.S. Cl. ...................................... 356/39; 356/73; 356/318; 250/461 B
[58] Field of Search ................... 356/39, 73, 317, 318; 250/458, 459, 461 B, 461 R

[56] References Cited

U.S. PATENT DOCUMENTS

| 3,916,197 | 10/1975 | Fulwyler | 350/461 B |
| 3,976,862 | 8/1976 | Curbelo | 356/39 |

*Primary Examiner*—Vincent P. McGraw
*Attorney, Agent, or Firm*—Spencer & Kaye

[57] ABSTRACT

In fluorescence analysis of multiply stained particles, particularly biological cells, in a continuous flow-through procedure, in which the particles are suspended in a carrier fluid, the carrier fluid containing the suspended particles is encased in a sheath stream, the resulting composite stream is conducted in laminar flow through an intensive laser light zone where fluorescent light pulses are generated by the action of the laser light on the particles and emanate from the particles, and those fluorescent pulses are detected and processed in real time in an electronic evaluation system, the laser light zone is produced by focussing at least two laser beams of respectively different wavelengths on two points spaced at a given distance apart along the path of the particle-containing fluid in the composite stream, and the detection and processing is effected by correlating the fluorescence pulses emanating from the two points on the basis of the spacing between the two points and of the flow speed of the stream, in order to evaluate only those pulses which correspond to the travel time of individual particles between the two points.

3 Claims, 4 Drawing Figures

FLUORESCENCE ANALYSIS OF STAINED PARTICLES

BACKGROUND OF THE INVENTION

The present invention relates to a method for the fluorescence analysis of multiply stained particles, particularly biological cells, in continuous flowthrough in which the particles are suspended in a carrier fluid, are then enclosed in an envelope, or sheath, stream and are conducted in laminar flow through an intensive laser light zone, where the fluorescent light pulses emanating from the particles are detected and processed in real time by an electronic evaluation system.

Methods of this type are described, for example, in the published article by H. Crissman, P. Mullaney and J. A. Steinkamp, entitled "Methods and Applications for Flow Systems for Analysis and Sorting of Mammalian Cells", in the publication *Methods in Cell Biology*, Volume 9, pp. 179-246 (1975), published by D. M. Prescott. The basic structure of the measuring arrangement is illustrated in a brochure entitled "Laser Review" of the firm Spectra-Physics, Mountain View, California, under the heading "New Laser System Used in Biomedical Studies".

If a plurality of components of a cell are to be analyzed simultaneously, particularly with respect to its chromosome content (DNA) and its protein content, the sample must be stained with different fluorescent dyes which each react specifically with one of the components, i.e. the DNA or the protein. It is known to use dyes for this purpose which have different fluorescence emission spectra at the same excitation frequency. However, this entails a certain limitation in the selection of suitable dyes, which may have a negative effect mainly on the sample preparation time involved and on the detection sensitivity. In addition, this technique requires the use of semitransparent mirrors and separating filters which also bring about intensity losses for the pulses received by the detectors.

SUMMARY OF THE INVENTION

It is an object of the present invention to improve the above-mentioned measuring method for the simultaneous analysis of a plurality of properties of particles so that no restrictions exist with respect to selection or combination of suitable dyestuffs.

A further object of the invention, therefore, is to create the possibility of using the optimum dyestuffs for each component involved.

Another object of the invention is to increase the detection sensitivity.

These and other objects according to the invention are achieved in a method and apparatus for the fluorescence analysis of multiply stained particles, particularly biological cells, in a continuous flowthrough procedure, in which the particles are suspended in a carrier fluid, the carrier fluid containing the suspended particles is then encased in a sheath stream, the resulting composite stream is conducted in laminar flow through an intensive laser light zone where fluorescent light pulses are generated by the laser light striking the particles and emanate from the particles, and the resulting fluorescent pulses are detected and processed in real time in an electronic evaluation system, by constituting the laser light zone of at least two laser beams of respectively different wavelengths, which beams are focussed on two points spaced at a given distance apart along the path of the particle-containing fluid in the composite stream, and by effecting the detection and processing by correlating the fluorescence pulses emanating from the two points on the basis of the space in between the two points and of the flow speed of the stream, in order to evaluate only those pulses which correspond to the travel time of individual particles between the two points.

A main advantage of the invention is that sample preparation times can be reduced from a previously required time of about 3 hours to less than 20 minutes. Moreover, the invention makes possible a free selection from a large stock of available dyestuffs, thus permitting selection of those dyestuffs which most intensively react with the particle component to be analyzed and are not accepted by the other sample components, particularly the foreign substances contained therein. This, together with the elimination of the need for mirrors and filters for the fluorescent light, simultaneously results in an increase in detection sensitivity.

DESCRIPTION OF THE PREFERRED EMBODIMENTS

Figure 1:
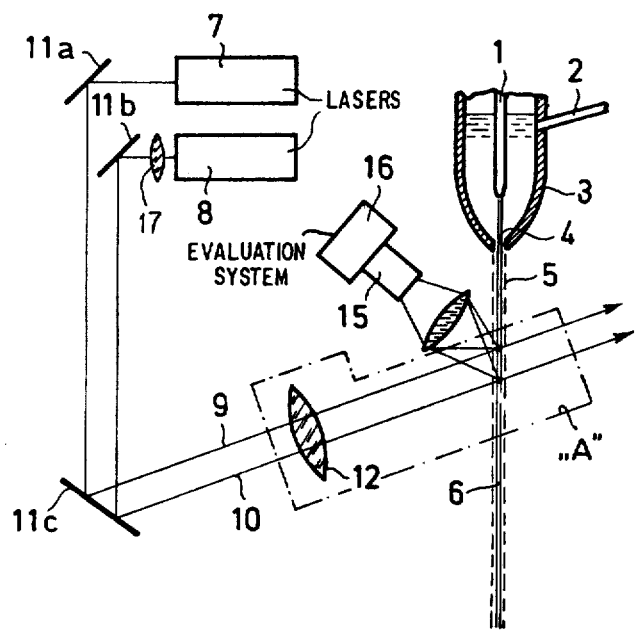
FIG. 1 is a schematic representation of the structure of measuring apparatus according to a preferred embodiment of the invention.
Figure 2:
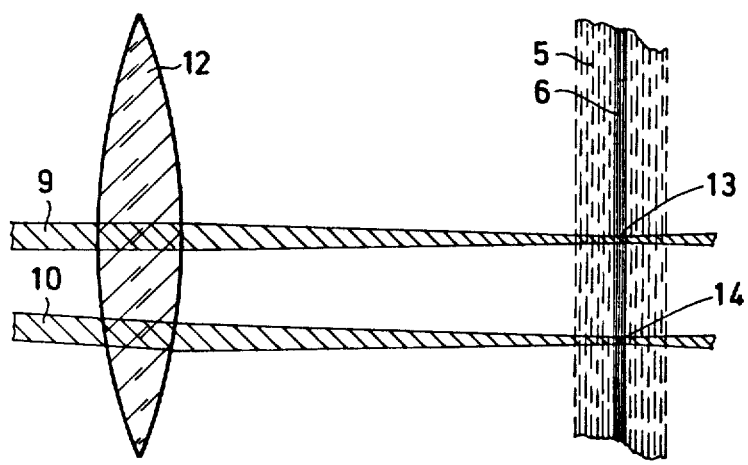
FIG. 2 is a cross-sectional detail view to an enlarged scale of region "A" of FIG. 1.

In the apparatus shown in FIG. 1, multiply stained biological cells suspended in a carrier fluid are conducted through a tube 1, and an electrolytic envelope, or sheath, fluid is conducted through tube 2, into a vessel 3. Vessel 3 is under pressure and has a fine, nozzle-shaped opening 4 of a diameter of about 50 to 100μ. The pressure in the tube 1 is somewhat higher than the pressure in tube 2 or in vessel 3, respectively, so that a laminar sample stream 6 enclosed in sheath stream 5 exits from nozzle 4, as is best seen in FIG. 2.

Two lasers 7 and 8 with different frequencies matched to the dyestuffs or their fluorescence spectra, respectively, serve as the radiation sources, the one beam 9 having a wavelength of, for example, 350 nm, the other beam 10 having a wavelength of 488 nm.

The two laser beams 9, 10 are deflected by fully-reflecting mirrors 11a, 11b and 11c and pass through a lens 12 approximately in parallel. Their divergence from parallelism is selected such that each beam is focussed by lens 12 in the center of the sample stream 6, but the two focal points 13 and 14 have a slight distance of about 0.5 mm from one another, as shown in FIG. 2, along the length of stream 6. At least mirrors 11a and 11b are pivotally mounted for permitting adjustment of the spacing between points 13 and 14. Lens 17 serves for the chromatic correction of lens 12 due to the different wavelengths of the laser beams used.

The resulting fluorescence pulses emitted by stained particles in the sample stream at the focal points are collected by a light-sensitive detector 15 and amplified in a downstream electronic evaluation system 16. A known pseudo-coincidence circuit evaluates only those pulses from the two focal points which follow one another at time intervals corresponding to the travel time of the individual cells from point 13 to point 14 in dependence on the spacing between the focal points 13 and 14 and on the flow speed of the sample stream 6. Thus two successive pulses meeting this requirement can be associated with one biologic cell, i.e. can be subjected to travel time cross correlation.

Figure 3:
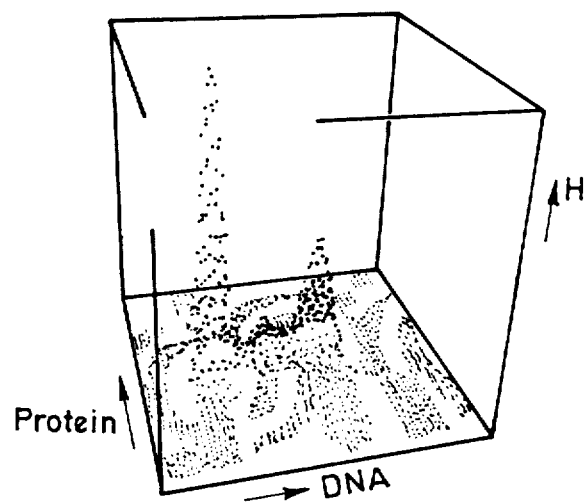
FIG. 3 is a three-dimensional diagram depicting the relative frequency of the DNA and protein content of a cancer cell-containing sample, the diagram having been produced with the use of fluorochromes producing different excitation and emission spectra.

The detector is a photomultiplier tube which is connected with an amplifier. The pulses arising sequentially in time are first amplified, then discriminated by electronic thresholding, followed by linear gating and streching (e.g. peak sensing and peak holding) by means of two linear gates and stretcher. The second gate is triggered by a delay unit which itself has been activated by the first pulse passed on to the gates from the amplifier. Untriggered at the time where the first pulse arises, the second gate ignores the first pulse and after having been triggered by the delay unit at the time where the second pulse arises, the second gate senses the second pulse. Thus, the first gate senses the first pulse and the second gate senses the second pulse. The first gate modified (extending the pulseoutput) so that the stretcher output is still there at the time when the second gate delivers the peak of the second pulse, so that the connected analog-to-digital converters are processed by coincidence FIG. 3 shows a characteristic frequency distribution H of cellular chromation, i.e. DNA per cell, and protein, i.e. protein per cell, of a sample containing cancer cells. The fluorochrome DAPI was used to stain the DNA and the fluorochrome SR 101 was used to stain the protein. In this example two dyes were used which had different excitation and emission spectra.

Figure 4:
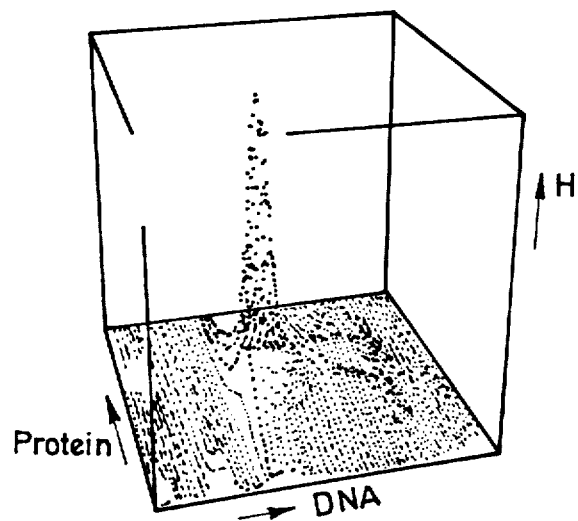
FIG. 4 is a diagram similar to that of FIG. 3 in which two fluorochromes were used as well which had different excitation frequencies but almost identical emission spectra.

In contrast, FIG. 4 is a diagram obtained when two fluorochromes, DAPI for DNA and NBD for protein, with different excitation spectra but with almost identical, nonseparable, greenish emission spectra were employed, which was not possible in the prior art.

It will be understood that the above description of the present invention is susceptible to various modifications, changes and adaptations, and the same are intended to be comprehended within the meaning and range of equivalents of the appended claims.

What is claimed is:

1. In apparatus for effecting fluorescence analysis of particles, dyed with two different dyestuffs in a continuous flowthrough procedure, by suspending the particles in a carrier fluid, forming the particle-containing carrier fluid into a sample stream and encasing the sample stream in a sheath stream, conducting the resulting composite stream in laminar flow through an intensive laser light zone where fluorescent light pulses are generated by the laser light and emanate from the particles, and detecting and processing the fluorescent light pulses in real time in an electronic evaluation system, the improvement comprising a focussing lens system for producing the laser light zone by focussing at least two laser beams of respectively different wavelengths, each wavelength being matched to a respectively different dyestuff or its fluorescence spectrum, on two points located at the center of the sample stream and spaced at a given distance apart along the path of the particle-containing fluid in the composite stream, said lens system being arranged to direct the laser beams normal to the sample stream with a slight divergence from one another, which divergence determines the spacing between the points at which the beams are focussed, and pivotally mounted deflection mirrors located upstream of said lens system for reflecting the laser beams onto said system and for adjusting the spacing between such points, and wherein said electronic evaluation system comprises means for correlating the fluorescent light pulses emanating from the two points on the basis of the spacing between the two points and of the flow speed of the stream, in order to evaluate only those pulses which correspond to the travel time of individual particles between the two points.

2. Apparatus as defined in claim 1 wherein the particles are biological cells.

3. Apparatus as defined in claim 1 further comprising two independent laser sources for producing the two laser beams.